United States Patent [19]

Ohda et al.

[11] Patent Number: 5,612,197
[45] Date of Patent: Mar. 18, 1997

[54] PROCESS FOR PRODUCING RECOMBINANT HUMAN SERUM ALBUMIN

[75] Inventors: Toyoo Ohda; Wataru Ohtani; Tomoshi Ohya; Shinobu Kuwae; Kenji Tomomitsu; Kaoru Kobayashi; Takao Ohmura, all of Osaka, Japan

[73] Assignee: The Green Cross Corporation, Osaka, Japan

[21] Appl. No.: 442,756

[22] Filed: May 17, 1995

[30] Foreign Application Priority Data

May 18, 1994 [JP] Japan .................................. 6-103994

[51] Int. Cl.$^6$ .......................... C12P 21/02; C07K 14/765
[52] U.S. Cl. .......................... 435/69.6; 435/69.1; 530/364
[58] Field of Search .................... 435/69.1, 69.6; 530/364

[56] References Cited

U.S. PATENT DOCUMENTS 5,294,699  3/1994  Ohmura et al. .................... 530/364
5,330,901  7/1994  Prevatt et al. .................... 435/69.1

OTHER PUBLICATIONS

Cook (ed.) "The chemistry and biology of yeasts", Academic Press, New York, N.Y. p. 171 (1958).
*Further Studies on the role of phenylalanine in gramicidin S biosynthesis by Bacillus brevis*, J-H. David Wu et al., Journal of Biotechnology, pp. 81–94.

*Primary Examiner*—Jasemine C. Chambers
*Assistant Examiner*—Scott D. Priebe
*Attorney, Agent, or Firm*—Sughrue, Mion, Zinn, Macpeak & Seas

[57] ABSTRACT

A process for producing recombinant human serum albumin is disclosed, which comprises culturing a human serum albumin-producing host, prepared by gene manipulation techniques in a medium that contains an amino acid, preferably at least one amino acid selected from the group consisting of alanine, aspartic acid, glutamic acid, histidine, serine, tryptophan, valine, isoleucine, phenylalanine, cysteine and arginine, more preferably histidine. The process can significantly increase the yield of human serum albumin over that produced by known processes.

17 Claims, No Drawings

PROCESS FOR PRODUCING RECOMBINANT HUMAN SERUM ALBUMIN

FIELD OF THE INVENTION

This invention relates to the improvement of a process for producing recombinant human serum albumin (to be referred to as "HSA" hereinafter) by culturing a host transformed by means of gene manipulation techniques.

BACKGROUND OF THE INVENTION

HSA is a main component of plasma proteins and is used in pharmaceutical preparations for the treatment of massive hemorrhage, shock, burn injury, hypoproteinemia, fetal erythroblastosis and the like.

Currently, HSA is produced mainly as a product from fractions of collected blood. However, such a production process is economically disadvantageous, and the supply of blood is sporadic. In addition, blood itself is also problematic in that it often contains undesirable substances such as hepatitis virus.

In order to solve such problems, attempts have been made to produce HSA by fermentation of microorganisms in which the HSA gene was introduced, thereby making use of the recently developing recombinant DNA techniques. However, even such recombinant DNA techniques cannot give satisfactory results in terms of the industrial mass production of HSA.

As a consequence, great concern has been directed toward the establishment of an industrial process for producing recombinant HSA in a large amount with a low cost.

SUMMARY OF THE INVENTION

An object of the present invention is to increase productivity of recombinant HSA in a process for the production thereof by means of gene engineering techniques, particularly to provide a large scale HSA production process which is effected by simple changes in the culture conditions of an HSA-producing host.

As a result of intensive investigation in order to solve the above-described problems, the present inventors have found that productivity of HSA can be increased when an HSA-producing host, prepared by gene manipulation techniques, is cultured in an amino acid-containing medium.

Thus, the present invention relates to a process for producing recombinant HSA which comprises culturing an HSA-producing host, prepared by gene manipulation techniques, in an amino acid-containing medium. More particularly, the present invention relates to a process for producing recombinant HSA, comprising:

(1) preparing a culture medium containing at least one amino acid selected from the group consisting of alanine (to be referred to as "Ala" hereinafter), aspartic acid (to be referred to as "Asp" hereinafter), arginine (to be referred to as "Arg" hereinafter), cysteine (to be referred to as "Cys" hereinafter), glutamic acid (to be referred to as "Glu" hereinafter), histidine (to be referred to as "His" hereinafter), isoleucine (to be referred to as "Ile" hereinafter), phenylalanine (to be referred to as "Phe" hereinafter), serine (to be referred to as "Ser" hereinafter), tryptophan (to be referred to as "Trp" hereinafter) and valine (to be referred to as "Val" hereinafter), and (2) culturing an HSA-producing host in said culture medium.

In another embodiment of the invention, the culture medium contains at least one amino acid selected from the group consisting of Ala, Asp, Glu, His, Ser, Phe, Trp and Val.

In a further embodiment of the invention, the culture medium contains at least one amino acid selected from the group consisting of Ala, Asp, His, Ser, Trp and Val.

In an additional embodiment of the invention, the culture medium contains at least one amino acid selected from the group consisting of Ala, Arg, His, Phe, Ser, Trp and Val.

In another embodiment of the invention, the culture medium contains His.

The culture medium contains the amino acid(s) as described in the media above in an amount of from 0.08 to 20 w/v %.

Additionally, the HSA-producing host may be a yeast strain.

DETAILED DESCRIPTION OF THE INVENTION

The HSA-producing host to be used in the present invention is not particularly limited, provided that it is a cellular host prepared via gene manipulation techniques. Any of the hosts disclosed in published reports, and those which will be developed in the future may be used. Illustrative examples of such hosts include microorganisms (*Escherichia coli*, a yeast strain, *Bacillus subtilis* and the like), as well as animal cells, which have been made into HSA-producing cells by gene manipulation techniques. According to the present invention, it is desirable to use as the host a strain of yeast, especially belonging to the genus Saccharomyces, such as *Saccharomyces cerevisiae*, the genus Pichia, such as *Pichia pastoris*, the genus Kluyveromyces, such as *Kluyveromyces lactis* or the genus Hansenula, such as *Hansenula polymorpha*. An auxotrophic strain or an antibiotic sensitive strain may also be used. Specific examples thereof include G418 sensitive strains such as *Saccharomyces cerevisiae* AH22 (a, his 4, leu 2, can 1), *Pichia pastoris* GTS115 (his 4) and *Kluyveromyces lactis* MW98-8c ($\alpha$, uraA, arg, lysK$^+$, pKD1$^0$). It is preferable to use *Pichia pastoris*, particularly *Pichia pastoris* GTS115.

Preparation of HSA-producing host, production of HSA by its culturing and isolation and recovery of HSA from the cultured broth are all carried out in accordance with known methods which may be modified slightly. For example, preparation of an HSA-producing host (or an HSA-producing strain) may be effected using a process in which a natural human serum albumin gene is used (JP-A-58-56684 corresponding to EP-A-73646, JP-A-58-90515 corresponding to EP-A-79739 and JP-A-58-150517 corresponding to EP-A-91527), a process in which a modified human serum albumin gene is used (JP-A-62-29985 and JP-A-1-98486 corresponding to EP-A-206733), a process in which a synthetic signal sequence is used (JP-A-1-240191 corresponding to EP-A-329127), a process in which a serum albumin signal sequence is used (JP-A-2-167095 corresponding to EP-A-319641), a process in which a recombinant plasmid is introduced into a chromosome (JP-A-3-72889 corresponding to EP-A-399455), a process in which hosts are fused (JP-A-3-53877 corresponding to EP-A-409156), a process in which a mutation is generated in a methanol containing medium, a process in which a mutant AOX2 promoter is used (EP-A-506040), a process in which HSA is expressed in *B. subtilis* (JP-A-62-215393 corresponding to EP-A-229712), a process in which HSA is expressed in yeast (JP-A-60-41487 corresponding to EP-A-123544, JP-A-63-

39576 corresponding to EP-A-248657 and JP-A-63-74493 corresponding to EP-A-251744) and a process in which HSA is expressed in Pichia (JP-A-2-104290 corresponding to EP-A-344459). (The term "JP-A" as used herein means an "unexamined published Japanese patent application")

Of these methods, the method in which mutation is induced in a methanol-containing medium is carried out in the following manner.

A transformant of an appropriate host, preferably a Pichia yeast, illustratively a strain GTS115 (NRRL deposition No. Y-15851), is obtained in the usual manner by introducing a plasmid, containing a transcription unit by which HSA is expressed under the control of the $AOX_1$ promoter, into the $AOX_1$ gene region of the host (cf. JP-A 2-104290). This transformant hardly grows in a medium containing methanol. In consequence, this transformant is cultured in a methanol-containing medium to generate mutation, and a strain capable of growing in the medium is isolated. Methanol concentration in the medium may range, for example, from 0.0001 to 5%. The medium may be either synthetic or natural. The culturing may be carried out, for example, at a temperature of from 15° to 40° C. for approximately from 1 to 1,000 hours.

Culturing of the HSA-producing host (namely the method for the production of HSA) may be effected by each of the methods disclosed in the above patents, by a method in which producer cells and the product are obtained in high concentrations by a fed-batch culture which method is carried out by gradually supplying a high concentration solution of glucose in appropriate small amounts to avoid high concentration substrate inhibition against the producer cells (JP-A-3-83595), by a method in which the HSA productivity is improved by the addition of fatty acids to the culture medium (JP-A-4-293495 corresponding to EP-A-504823 and U.S. Pat. No. 5,334,512) or by a method in which coloring of HSA is inhibited by culturing a host in the presence of diamines and the like (JP-A-5-260986 corresponding to EP-A-591605 and U.S. Pat. No. 5,369,020).

The medium to be used in the production process of the present invention is an amino acid-containing medium, especially a medium which contains at least 1 amino acid selected from neutral amino acids such as glycine (to be referred to as "Gly" hereinafter), Ala, Ser, Val, leucine (to be referred to as "Leu" hereinafter), Ile, Cys, Phe, Trp or Proline (to be referred to as "Pro" hereinafter), acidic amino acids such as Asp or Glu and basic amino acids such as Arg or His. An example of a medium capable of markedly increasing HSA productivity when used in the culturing of an HSA-producing host is a medium which contains at least 1 amino acid selected from the group consisting of Ala, Arg, Asp, Glu, Gly, His, Phe, Ser, Trp, Cys, Ile and Val, preferably a medium which contains at least 1 amino acid selected from the group consisting of Ala, Asp, Glu, His, Phe, Ser, Trp and Val, more preferably a medium which contains at least 1 amino acid selected from the group consisting of Ala, Asp, His, Ser, Trp and Val. On the other hand, in comparison with an amino acid-free medium, a medium which contains at least 1 amino acid selected from the group consisting of Ala, Arg, His, Ser, Trp, Phe, and Val is effective in producing HSA in a large quantity without allowing an HSA-producing host itself to grow when used in the culturing of the host. Production of a large quantity of HSA by not allowing the host cells themselves to grow significantly is advantageous especially in the case of an expression system in which HSA is allowed to secrete into culture supernatant, because the ratio of culture supernatant to the amount of culture broth (medium) becomes large so that HSA can be recovered in a higher yield.

A medium which contains His is particularly preferred as the medium to be used in the present invention. This medium is especially good for improving productivity of HSA, because it can considerably increase production yield of HSA independent of the growth of the HSA-producing host itself.

The medium to be used in the present invention may contain the above-described amino acid alone or as a mixture of two or more amino acids.

The amino acid content of the medium may range, for example, from about 0.08 to 20 w/v %, preferably from about 0.1 to 1 w/v %.

Other components of the medium to be used in the present invention are not particularly limited, provided that the medium contains at least one of the above-described amino acids. Examples of other components are those which are contained in known culture media generally used in this field. In general, various sugars are used as carbon sources, urea, ammonium salts, nitrates and the like are used as nitrogen sources and various vitamins, nucleotides and the like are used as trace nutrients, as well as inorganic salts such as of Mg, Ca, Fe, Na, K, Mn, Co, Cu and the like.

Illustrative examples of the useful medium include YNB liquid medium (0.7% Yeast Nitrogen Base without amino acids (manufactured by Difco) and 2% glucose), MeOH-ammonium acetate medium (composition: cf. Examples), YPD liquid medium (1% Yeast Extract (Difco), 2% Bacto-peptone (Difco) and 2% glucose) and the like. When the HSA-producing host is a methanol assimilating strain, a methanol-containing medium may be used. In that case, the methanol concentration may range approximately from 0.01 to 5%.

In other words, the medium to be used in the present invention can be prepared easily, by adding the above-described amino acid(s) to any known medium.

The pH of the medium may be neutral, slightly basic or slightly acidic. Preferably, the medium may have a pH value of from about 5.7 to 6.5.

Culture conditions may be selected in the usual way.

The culture temperature may range, for example, generally from about 15° to 43° C. It may range from about 20° to 37° C. when the host is a bacterium. It may range from about 20° to 30° C. when the host is a yeast. Particularly, the yeast host may be cultured at a temperature of generally from 21° to 29° C., preferably 21° to 28° C., more preferably 23° to 28° C., most preferably 25° to 27° C. The culture period is approximately from 1 to 1,000 hours.

It is desirable to carry out a seed culturing prior to the main culturing making use of, for example, the above-described YNB or YPD liquid medium. Preferably, the seed culturing may be carried out for, for example, about 10 to 100 hours preferably at about 30° C. in the case of yeast strains or about 37° C. in the case of bacterial strains. The above-described amino acid(s) may also be used in the seed culturing.

After completion of the culturing, HSA is collected from the culture supernatant (filtrate) or cells by isolation and purification means commonly known. Illustrative examples of such means include a method in which HSA is purified by subjecting a culture supernatant (filtrate) to ultrafiltration, heat treatment, acid treatment and ultrafiltration, in that order, and then to respective treatments with cation exchanger, hydrophobic chromatography and anion exchanger (JP-A-5-317079 corresponding to EP-A-570916) and a method in which HSA is decolorized by chelate resin treatment (JP-A-5-328991 corresponding to EP-A-570916).

The following examples are provided to further illustrate the present invention, but are not to be understood as limiting the scope of the present invention.

EXAMPLE 1

(1) Preparation of strain to be used

A strain of *Pichia pastoris*, PC4130, has been obtained in accordance with the method disclosed in JP-A-2-104290, by substituting the $AOX_1$ gene region of *P. pastoris* GTS115 (his 4) with a NotI-digested fragment of plasmid pPGP1 which contains a transcription unit by which HSA is expressed under the control of the $AOX_1$ promoter. Because of the absence of the $AOX_1$ gene, this strain has a reduced ability to grow on a medium which contains methanol as the carbon source (methanol assimilation negative strain; to be referred to as "Mut⁻ strain" hereinafter).

The strain PC4130 was inoculated into 3 ml of YPD medium (1% yeast extract, 2% Bacto Peptone and 2% glucose). After 24 hours of culturing, the cells were inoculated into 50 ml of YPD medium so that the cell density was adjusted to initial turbidity with an $OD_{540}$ of 0.1. After 3 days of culturing at 30° C., the resulting cells again were inoculated into 50 ml of YPD medium at an initial cell turbidity of 0.1 at $OD_{540}$. Thereafter, subculturing was repeated every 3 days in the same manner. After each subculturing, cells were diluted with sterile water and poured onto a 2% MeOH-YNBw/oa.a. plate (0.7% Yeast Nitrogen Base without Amino Acids, 2% methanol and 1.5% agar powder) in an inoculum size of $10^7$ cells/plate, followed by 5 days of culturing at 30° C. to judge the presence/absence of colonies. Twenty colonies were found on the 2% MeOH-YNBw/oa.a. plate after 12 days of the successive subculturing. Mut⁻ strains hardly grow on the 2% MeOH-YNBw/oa.a. medium, while Mut⁺ strains (methanol assimilation positive strains) grow well. That is, the presence of a colony means that the strain acquired the capacity of increased methanol assimilation and thus a Mut⁺ strain was obtained. One of the thus obtained colonies was diluted appropriately with sterile water and spread onto a 2% MeOH-YNBw/oa.a. plate to isolate single colonies. One of the resulting single colonies was named GCP101.

An HSA expression plasmid pMM042 was constructed using an $AOX_2$ promoter (a mutant of the natural $AOX_2$ promoter (*YEAST*, 5, 167–177, 1988; *Mol. Cell. Biol.*, 4, 1316–1323, 1989), in which the 255th base upstream from the initiation codon of said promoter is changed from T to C) isolated from the above-described strain GCP101. The thus constructed plasmid was introduced into *Pichia pastoris* GTS115 to obtain a transformant UHG42-3 (JP-A-4-299984 or EP-A-506040).

(2) Medium composition

YPD medium (2% Bacto-peptone, 1% yeast extract and 2% glucose) was used for the seed culture. A MeOH-ammonium acetate medium shown in Table 1 was used in the main culture.

TABLE 1

| Composition of MeOH-ammonium acetate medium | |
|---|---|
| Component | Concentration (mg/l) |
| Methanol | 40 ml |
| Glycerol | 1,000 |
| $CH_3COONH_4$ | 5,000 |
| $KH_2PO_4$ | 10,000 |
| $CaCl_2\ 2H_2O$ | 100 |

TABLE 1-continued

| Composition of MeOH-ammonium acetate medium | |
|---|---|
| Component | Concentration (mg/l) |
| KCl | 2,000 |
| NaCl | 100 |
| $MgSO_4\ 7H_2O$ | 2,000 |
| $ZnSO_4\ 7H_2O$ | 100 |
| $CuSO_4\ 5H_2O$ | 5 |
| $FeCl_3\ 6H_2O$ | 100 |
| Biotin | 0.1 |
| Vitamin $B_1$ | 10 |
| Vitamin $B_6$ | 1 |
| Sodium pantothenate | 10 |
| Inositol | 50 |

(3) Culturing method i) Seed culture

A 1 ml portion of the strain contained in a freeze-dried stock vial was inoculated into a 300-ml baffled Erlenmeyer flask containing 50 ml of YPD medium and cultured at 30° C. for 24 hours with shaking.

ii) Main culture

A 1 ml portion of the seed culture medium was inoculated into a 300-ml baffled Erlenmeyer flask containing 50 ml of the MeOH-ammonium acetate medium which had been supplemented with each amino acid to give a final concentration of 0.1% and adjusted to pH 6.0, and cultured at 30° C. for 89 hours with shaking.

REFERENCE EXAMPLE 1

Measurement of cell density

During the main culturing carried out in Example 1 (3) ii), the culture broth was sampled at optional intervals, each of the thus collected samples was diluted with distilled water to give the $OD_{540}$ value of 0.3 or less at the time of measurement, and then absorbance of the diluted sample at 540 nm was measured using a spectrophotometer (UV 200, manufactured by Shimadzu Corp.).

REFERENCE EXAMPLE 2

Evaluation of rHSA productivity

The entire portion of the culture broth after completion of the culturing was recovered and subjected to 20 minutes of centrifugation at 3,000 rpm. The resulting supernatant was clarified by filtering it through MILLEX-HV (Millipore Corp.; 0.45 μm), and a 15 ml portion of the resulting filtrate was concentrated about 20-fold using Amicon CentriPrep 10 (molecular weight cutoff of 10,000, manufactured by Amicon Corp.) (4° C., 3,000 rpm, about 6 hours) and then subjected to HPLC gel filtration analysis under the following conditions to evaluate HSA productivity:

Column: TSK gel $G3000SW_{xl}$ (Tosoh Corp.)

Mobile phase: 0.3 M NaCl, 50 mM Na-Phosphate, 0.1% $NAN_3$, pH 6.5

Flow rate: 0.7 ml/min

Injection: 50 μl

Detection: $A_{280}$, $A_{350}$ (dual wave length)

REFERENCE EXAMPLE 3

Evaluation of coloring degree of produced HSA $A_{350}/A_{280}$ values were calculated using the results of the HPLC gel filtration analysis carried out for the evaluation of HSA productivity, and these values were used for the evaluation of coloring degree of HSA produced by the process of the present invention.

TEST EXAMPLE 1

Effects of each amino acid contained in the medium were examined. Amino acid content of the medium was fixed to 0.1 w/v %. Other conditions including culture conditions were as described in Example 1. The results are shown in Tables 2 to 4. Productivity of HSA, amount of cells and degree of coloring are respectively shown by percentage based on the case of no amino acid addition as 100%.

TABLE 2

| Amino acid and other components | Yield (%) | Cell Yield (%) | Coloring degree (%) |
|---|---|---|---|
| Control | 100 | 100 | 100 |
| Yeast extract | 157 | 118 | 127 |
| Peptone | 122 | 120 | 122 |
| Gly | 127 | 123 | 145 |
| Ala | 220 | 99 | 112 |
| Asp | 258 | 111 | 135 |
| Arg | 132 | 98 | 125 |
| Glu | 173 | 109 | 145 |
| His | 410 | 76 | 96 |
| Ile | 144 | 105 | 118 |
| Lys | 42 | 83 | 104 |
| Met | 28 | 24 | 124 |

TABLE 3

| Amino acid and other components | Yield (%) | Cell yield (%) | Coloring degree (%) |
|---|---|---|---|
| Control | 100 | 100 | 100 |
| His | 439 | 65 | 72 |
| Lys | 21 | 44 | 97 |
| Ala | 146 | 103 | 109 |
| Asp | 221 | 107 | 131 |
| Trp | 238 | 91 | 215 |
| Val | 235 | 87 | 102 |
| Leu | 117 | 102 | 111 |
| Ser | 200 | 91 | 105 |
| Thr | 105 | 103 | 137 |
| Asn | 119 | 121 | 139 |
| Gln | 78 | 113 | 105 |
| Pro | 114 | 115 | 135 |
| Ca pantothenate | 72 | 106 | 120 |

TABLE 4

| Amino acid | Yield (%) | Cell yield (%) | Coloring degree (%) |
|---|---|---|---|
| Control | 100% | 100% | 100% |
| Phe | 165 | 89 | 112 |
| Cys | 134 | 98 | 161 |

TEST EXAMPLE 2

Effects of amino acid concentrations (0.01 to 1 w/v %) in the medium were examined. His was used as the amino acid. Other conditions including culturing conditions were as described in Inventive Example 1. The results are shown in Table 5.

TABLE 5

| Amino acid | Concentration % (w/v) | Yield (%) | Cell Yield (%) | Coloring degree (%) |
|---|---|---|---|---|
| Control |  | 100 | 100 | 100 |
| His | 0.1 | 326 | 82 | 112 |
| His | 0.2 | 214 | 67 | 88 |
| His | 0.3 | 188 | 86 | 71 |
| His | 0.4 | 185 | 89 | 71 |
| His | 0.6 | 159 | 71 | 76 |
| His | 1.0 | 133 | 85 | 71 |

As is evident from the above test results, yield of HSA can be increased significantly when an HSA-producing host is cultured in a medium which contains an amino acid, especially Ala, Asp, Glu, His, Phe, Trp, Val or Ser. When compared with an amino acid-free culture system, it was found that the HSA yield-increasing effect of a medium which contains Ala, His, Phe, Trp, Val or Ser or a medium which contains Arg or Cys was not due to an increase in the cell yield.

According to the present invention, yield of HSA by an HSA-producing host prepared by gene manipulation techniques can be increased by employing a process which can be carried out easily with a relatively low cost by simply changing culture conditions. In particular, the HSA production yield can be increased 1.5 to 5 times in comparison with the case of culturing with no supplement of amino acids, when cultured using a medium which contains at least one amino acid selected from Ala, Asp, Glu, His, Phe, Trp, Val and Ser. In addition, according to a process which uses a medium supplemented with at least one amino acid selected from Ala, His, Phe, Trp, Val, Ser, Arg and Cys, the HSA production yield can be increased 1.3 to 5 times independent of the cell growth. Such an effect is particularly significant in a His-containing medium. Also, the HSA productivity-increasing effect can be obtained even with a relatively small amino acid content of 0.08 to 1 w/v %. In addition, some of the above-described amino acids can reduce coloring of the produced HSA.

On the basis of these effects, the HSA production process of the present invention can be regarded as practically useful.

While the instant invention has been described in detail and with reference to specific embodiments thereof, it will be apparent to one skilled in the art that various changes and modifications can be made therein without departing from the spirit and scope thereof.

What is claimed is:

1. A process for producing recombinant human serum albumin which comprises culturing a human serum albumin-producing host, prepared by gene manipulation techniques, in a medium supplemented with at least one amino acid selected from the group consisting of alanine, aspartic acid, arginine, cysteine, glutamic acid, histidine, isoleucine, phenylalanine, serine, tryptophan and valine, with the proviso that no other amino acids are present in said medium and that said human serum albumin-producing host would grow in said medium not supplemented with the at least one amino acid.

2. The process for producing recombinant human serum albumin according to claim 1 wherein the at least one amino acid is selected from the group consisting of alanine, aspartic acid, glutamic acid, histidine, serine, phenylalanine, tryptophan and valine.

3. The process for producing recombinant human serum albumin according to claim 1 wherein the at least one amino acid is selected from the group consisting of alanine, aspartic acid, histidine, serine, tryptophan and valine.

4. The process for producing recombinant human serum albumin according to claim 1 wherein the at least one amino acid is selected from the group consisting of alanine, arginine, histidine, phenylalanine, serine, tryptophan and valine.

5. The process for producing recombinant human serum albumin according to claim 1 wherein the at least one amino acid is histidine.

6. The process for producing recombinant human serum albumin according to claim 1 wherein said medium contains said at least one amino acid in an amount of 0.08 to 20 w/v %.

7. The process for producing recombinant human serum albumin according to claim 1 wherein said medium contains said at least one amino acid in an amount of 0.1 to 1.0 w/v %.

8. The process for producing recombinant human serum albumin according to claim 1 wherein said human serum albumin-producing host is a microorganism or an animal cell.

9. The process of claim 8 wherein said microorganism is a yeast strain.

10. The process of claim 8 wherein said microorganism is selected from the group consisting of *Escherichia coli*, a yeast strain, and *Bacillus subtilis*.

11. The process of claim 9 wherein said yeast strain is a member of the genus Saccharomyces, Pichia or Hansenula.

12. The process of claim 11 wherein said member of said genus Saccharomyces is derived from *Saccharomyces cerevisiae* AH22.

13. The process of claim 11 wherein said member of said genus Pichia is derived from *Pichia pastoris* GTS115.

14. A process for producing recombinant human serum albumin which comprises culturing a human serum albumin-producing host, prepared by gene manipulation techniques, in a medium supplemented with at least one amino acid selected from the group consisting of alanine, aspartic acid, arginine, cysteine, glutamic acid, histidine, isoleucine, phenylalanine, serine, tryptophan and valine wherein said human serum albumin producing host would grow in said medium not supplemented with the at least one amino acid.

15. The process according to claim 14 wherein addition of the at least one amino acid enhances production of said recombinant human serum albumin without a corresponding increase in the quantity of the human serum albumin-producing host.

16. The process according to claim 1, wherein the at least one amino acid is not required for growth of said host.

17. The process according to claim 14, wherein the at least one amino acid is not required for growth of said host.

* * * * *